United States Patent
Roth (10) Patent No.: US 6,676,802 B2
(45) Date of Patent: Jan. 13, 2004

(54) REMOTE EXPOSURE OF WORKPIECES USING A PLASMA

(75) Inventor: J. Reece Roth, Knoxville, TN (US)

(73) Assignee: Universtiy of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 10/156,394

(22) Filed: May 28, 2002

(65) Prior Publication Data

US 2003/0029566 A1 Feb. 13, 2003

Related U.S. Application Data

(62) Division of application No. 09/362,471, filed on Jul. 28, 1999, now Pat. No. 6,406,759.
(60) Provisional application No. 60/070,779, filed on Jan. 8, 1998, and provisional application No. 60/082,645, filed on Apr. 22, 1998.

(30) Foreign Application Priority Data

Jan. 8, 1999 (WO) ............................. PCT/US99/00430

(51) Int. Cl.[7] ........................... H05H 1/00; C23C 16/00
(52) U.S. Cl. ........................... 156/345.35; 156/345.33; 118/715; 118/723 ER; 118/723 IR; 118/723 ME
(58) Field of Search ....................... 156/345.35, 345.33, 156/345.36, 345.34; 118/715, 723 ER, 723 IR, 723 ME (56) References Cited

U.S. PATENT DOCUMENTS

| | | | |
|---|---|---|---|
| 4,381,965 A | 5/1983 | Maher, Jr. et al. | |
| 4,472,756 A | 9/1984 | Masuda | |
| 4,585,668 A | 4/1986 | Asmussen et al. | 427/130 |
| 5,082,517 A | 1/1992 | Moslehi | 438/130 |

(List continued on next page.)

FOREIGN PATENT DOCUMENTS

| | | |
|---|---|---|
| DE | 196 05 226 A | 8/1997 |
| EP | 0063273 A | 10/1982 |
| EP | 588 486 A | 3/1994 |
| GB | 2 254 185 A | 9/1992 |
| JP | 3-219082 | 9/1991 |
| WO | WO 9638311 | 12/1996 |

OTHER PUBLICATIONS

"Multiple Electrode Plasma Accelerate Incorporate Odd Number Extra Gas Permeable Electrode Main Electrode Alternate Connect Power Source Earth", by Kolchenko A I, Derwent Publications Ltd., Jan. 1987, 87–275756. for patent SU 1282366 A published 1/87).

Patent abstracts of Japan, Publication No. 03219082, by Horiike Yasuhiro, published Sep., 1991.

*Primary Examiner*—Parviz Hassanzadeh
(74) *Attorney, Agent, or Firm*—Steve Mendelsohn (57) ABSTRACT

An OAUGD plasma is generated using, for example, paraelectric or peristaltic electrohydrodynamic (EHD) techniques, in the plasma generator of a remote-exposure reactor, wherein one or more active species, especially oxidizing species in the plasma are convected away from the plasma-generation region and directed towards a workpiece that is located outside of the plasma-generation region (e.g., within an optional remote-exposure chamber configured to the plasma generator). In this way, the workpiece can be subjected to the one or more active species without directly being subjected to either the plasma or to the electric fields used to generate the plasma. The plasma generator may have a set of flat panels arranged within an air baffle to convect the active species in a serpentine manner through the plasma generator. The remote-exposure reactor can also be configured as a portable backpack unit with tubing that is used to direct the active species onto the workpiece, rather than placing the workpiece within a remote-exposure chamber of the reactor.

12 Claims, 7 Drawing Sheets

U.S. PATENT DOCUMENTS

| | | |
|---|---|---|
| 5,089,441 A | 2/1992 | Moslehi ........................ 438/130 |
| 5,387,842 A | 2/1995 | Roth et al. ............... 315/111.21 |
| 5,403,453 A | 4/1995 | Roth et al. ................... 204/164 |
| 5,414,324 A | 5/1995 | Roth et al. ............... 315/111.21 |
| 5,610,097 A | 3/1997 | Shimizu |
| 5,669,583 A | 9/1997 | Roth ........................... 244/130 |
| 5,779,991 A | 7/1998 | Jenkins |
| 5,928,527 A | 7/1999 | Li et al. ........................ 216/67 |
| 5,941,448 A | 8/1999 | Sindzingre et al. ........... 134/1.1 |
| 6,083,355 A | 7/2000 | Spence ........................ 204/164 |
| 6,106,659 A | 8/2000 | Spence et al. ................. 216/71 |
| 6,156,114 A | 12/2000 | Bell et al. .................... 427/562 |
| 6,194,036 B1 | 2/2001 | Babayan et al. ............. 427/563 |
| 6,238,587 B1 | 5/2001 | Siniaguine et al. ............ 216/67 |
| 6,287,976 B1 | 9/2001 | Siniaguine et al. .......... 427/569 |

(a) Plasma Off

FIG. 1A (b) Plasma On, E ~ 4.5 kV rms, F = 3 kHz

REMOTE EXPOSURE OF WORKPIECES USING A PLASMA

CROSS-REFERENCE TO RELATED APPLICATIONS

This is a divisional of applicatian serial No. 09/362,471 filed on Jul. 28, 1999 now U.S. Pat. No. 6,406,759. This application claims the benefit of the filing date of U.S. provisional application No. 60/070,779, filed Jan. 8, 1998 and U.S. provisional application No. 60/082,645, filed on Apr. 22, 1998.

BACKGROUND OF THE INVENTION

1. Field of the Invention

The present invention relates to cold, non-equilibrium glow discharge plasmas, particularly those at or about atmospheric pressure.

2. Background Literature and Patent References

Industrial Plasma Engineering, Volume 1—Principles. Institute of Physics Press, Bristol, UK ISBN 0-7503-0318-2, provides comprehensive and thorough information on several aspects of plasma technology. The book is incorporated herein by reference.

Informative patents that also provide background information are the following: U.S. Pat. Nos. 5,387,842, 5,669,583, 5,414,324, 5,403,453, 5,456,972, which are incorporated herein by reference.

3. Description of the Related Art

It is well known to expose a workpiece to a glow discharge plasma to change one or more properties of the workpiece. For example, it is known to generate a glow discharge plasma between two parallel-plate electrodes, and to pass a continuous web or film between the electrodes and therefore through the discharge plasma to change, e.g., the wettability of the web or film. In such situations, the workpiece is exposed to the discharge plasma in the same region in which the plasma is generated. In some circumstances, however, this so-called direct exposure to the plasma may result in a high-power flux of active species which may heat and damage the workpiece surface, but which does not contribute to the desired effects. In addition, direct exposure to the plasma may cause the workpiece to be bombarded by all active species, including electrons, ions, ultraviolet radiation, ozone, and molecular fragments, some of which may be damaging or unhelpful to achieving the desired result of exposure to a particular active species.

Moreover, direct exposure implies subjecting the workpiece to the same electromagnetic fields that are used to generate the plasma, which again may be detrimental to the workpiece. For example, generating atmospheric plasmas may require electric fields of at least several kilovolts per centimeter in order to maintain a plasma at one atmosphere (e.g., a minimum of 8.5 kilovolts per centimeter in air for a one-atmosphere uniform glow discharge (OAUGD) plasma). When the plasma-generation region is a space between two parallel plates, the immersion of a reasonably large workpiece in the plasma between such parallel plates can require voltages so high that they become a serious occupational safety hazard to those using the equipment (e.g., due to sparking, X-ray production, and radio frequency (RF) interference). Such hazards may make such a unit impractical, for example, for use as sterilization units for medical or dental offices.

SUMMARY OF THE INVENTION

The present invention is directed to techniques for remotely exposing workpieces to OAUGD plasmas. According to these techniques, some of the plasma active species are propelled from the region in which the plasma is generated into a remote region where the workpiece is positioned for exposure to one or more constituents of the plasma without necessarily exposing the workpiece to all of the plasma constituents or to the strong electric fields within the plasma-generation region. According to the present invention, the active species are convected by any suitable means from the plasma-generation region to the remote-exposure region without necessarily requiring an external force to be applied to move the plasma.

Plasmas like the OAUGD plasma can benefit by decoupling the plasma-generation region from the remote-exposure region in which a workpiece is exposed to the active species that do the work of plasma processing. Such a remote-exposure reactor not only enables the generation of plasma-active species at one atmosphere without expensive vacuum systems, but it also enables the convection of active species, e.g., for sterilization or increasing the surface energy of materials, away from the plasma-generation region into a remote chamber where objects of any size, shape, or porosity can be treated without respect to the plasma operating conditions, including the required operating voltage. Active species can include ultraviolet or visible photons; charged particles, including electrons, ions and free radicals; and highly reactive neutral species, such as reactive atoms (oxygen, fluorine, ozone, nitrogen oxides, etc.), excited atomic states, and reactive molecular fragments, such as monomers.

In the present invention the active species which produce the desired effect are convected by the neutral gas flow away from the plasma generating regions, where the surfaces may experience a flux of detrimental active species. Thus, an effect of the invention is the convection of desired active species such as oxidizing species, like atomic oxygen, ozone, nitrogen oxides, away from the region of high heat fluxes, ultraviolet radiation, and strong electric fields where the plasma is generated.

The ability to decouple the generation of the plasma from the exposure site of the workpiece will greatly enhance the utility of the OAUGD plasma technology and open up many industrial uses that would otherwise either be difficult to implement, or difficult to sell to potential customers.

In one embodiment, the present invention is a method for treating a workpiece with one or more active species from a plasma, comprising the steps of (a) applying power to generate an electric field within a plasma-generation region to generate a volumetric plasma; (b) convecting the one or more active species away from the plasma-generation region as a result; by one of the selected means, such as a blower, and (c) subjecting the workpiece to the one or more active species, wherein the workpiece is located outside of the plasma-generation region such that the workpiece is not directly subjected to the plasma or to the electric field within the plasma-generation region.

In an alternative embodiment, the present invention is a remote-exposure reactor, comprising (a) a plasma generator defining a plasma-generation region and having one or more plasma panels adapted to be configured to a power supply to generate a plasma within the plasma-generation region, wherein one or more active species of the plasma are convected away from the plasma-generation region as a result of the means of propelling the plasma; and (b) means for subjecting a workpiece located outside of the plasma-generation region to the one or more active species such that the workpiece is not directly subjected to the plasma or to the electric field within the plasma-generation region.

BRIEF DESCRIPTION OF THE DRAWINGS

Other aspects, features, and advantages of the present invention will become more fully apparent from the following detailed description, the appended claims, and the accompanying drawings in which:

DETAILED DESCRIPTION

In general, a remote-exposure reactor is a plasma reactor capable of exposing one or more workpieces to the active species generated by a plasma, without directly exposing the workpiece itself to the plasma or to the high surface heat fluxes or electric fields within the plasma-generation region. The present invention can be implemented as a remote-exposure reactor using flat-panel electrodes to generate a one-atmosphere uniform glow discharge (OAUGD) surface plasma or by generating an OAUGD in the volume between two parallel plates. In such a remote-exposure reactor, the plasma-generation region is decoupled or separated from the chamber in which the workpiece is exposed to the active species generated by the plasma. This is done by generating a forced convection of the neutral gas or by generating a self-propelled plasma in the plasma-generation region which causes the active species to convect from the plasma-generation region to a remote chamber in which the workpiece is exposed to those active species. Such remote exposure is desirable, because the generation of, e.g., an OAUGD plasma between parallel plate or strip electrodes is limited by the required electric field, which is approximately 2 to 3 kilovolts per centimeter for argon and helium, and is at least 8.5 kilovolts per centimeter for air. In a parallel-plate or strip-electrode OAUGD plasma reactor, these electric fields quickly lead to either unacceptably high RF voltages, or to reactors (and workpieces) the sizes of which are limited by the maximum voltage dictated by considerations of safety and/or convenience.

In the case of the OAUGD plasma, as is true of industrial plasma processing technology in general, there has been a need to be able to decouple the exposure of large or bulky workpieces from the region in which the plasma itself and its active species are generated. This has been done to a very limited extent with low-pressure plasmas for both sterilization, and for remote plasma-assisted chemical vapor deposition (PCVD) applications, but has not been done before with the active species from plasmas generated at one atmosphere. The industrial and commercial applications of such a remote-exposure reactor will be significant, particularly in the fields of sterilization of medical equipment, in treating microelectronic circuit boards and components, and in treating the surfaces of films and fabrics.

Industrial Uses of a Remote Exposure Reactor Based on the OAUGD Plasma

The following presents a non-exhaustive list of potential applications for a remote-exposure reactor based on a plasma such as the OAUGD plasma.

1) Sterilization/decontamination units. Such sterilization and decontamination units could be used for the decontamination of surfaces compromised by chemical agents and/or for the sterilization of surfaces compromised by toxic biological agents. Microorganisms can be killed in a remote-exposure reactor. A remote-exposure configuration would allow, for example, various equipment such as personal items, clothing, etc., to be decontaminated or sterilized by putting the items in a large-volume version of the remote-exposure reactor, and exposing them for a few minutes to active species that will sterilize or decontaminate them. Beyond that, a configuration involving a remote-exposure reactor carried in a backpack with rechargeable batteries and a power supply could be built in a "leaf blower" configuration, in which the active species are blown through a long tube to the surfaces of equipment, like the interior of an aircraft cockpit or the interior of a vehicle that had to be decontaminated. Both a remote-exposure chamber and a portable "leaf blower" unit could also be used to deal with hazardous, toxic, or biohazard spills that occur in civilian and workplace contexts.

2) Treatment of electronic circuit boards. The active species from a remote-exposure reactor could be used to treat electronic circuit boards and microelectronic chips without danger of having sensitive electronic components on such boards damaged by the high electric fields associated with direct exposure to the OAUGD plasma, as is now the case. "Live" microelectronic chips can be exposed to the OAUGD plasma operating with air without damage from direct exposure to the OAUGD plasma to microelectronic chips and other sensitive components on the circuit boards. With the remote-exposure reactor, the surface energy of the electrical contacts and other components can be increased by exposing them to the active species in a region that has no electric fields, and poses no possibility of electrical sparking.

3) Increasing the surface energy of films and fabrics. A remote-exposure reactor could deliver active species on the surface of thin and heat-sensitive plastic films and fabrics without disturbing or damaging their bulk material. In direct-exposure applications, it sometimes becomes difficult to prevent occasional plasma filaments from developing at the edges of the workpiece, the electrode edges, or the edges of the web when a workpiece is directly exposed to the plasma. On the other hand, if the active species which increase the surface energy can be convected to the workpiece from the plasma-generating region, this would allow a great deal more flexibility in the design of the industrial equipment intended to utilize the OAUGD plasma. Such applications might involve increasing the surface energy of films and fabrics for increased wettability, wickability, printing, and printing with water-based inks.

4) Medical and Dental Sterilization Units. A remote-exposure reactor could be used to sterilize medical instruments after operations, bandages, dental tools, and other medical and dental equipment. By using a remote-exposure reactor, it would make little difference whether the object to be sterilized is electrically conducting or insulating, and it also would make relatively little difference how large or small it was, as it is not necessary to immerse the object in plasma in order to sterilize it in the exposure chamber of a remote-exposure reactor. It should be possible to make a remote-exposure reactor for use in medical and dental clinics about the same size and about the same cost as an ordinary microwave oven. The unit itself would require only a few plasma-generating panels, a low-frequency, high-voltage RF power supply, a few control functions, and the rest is inexpensive sheet metal.

5) Plasma chemical vapor deposition. One can do plasma chemical vapor deposition (PCVD) with a remote-exposure reactor by generating a precursor for a layer to be deposited in the plasma region, and then convecting the precursor active species to the workpiece where a chemically deposited layer is built-up on the surface. Remote deposition is already done to a limited extent in low-pressure vacuum systems, but such remote-exposure PCVD has not been done anywhere with atmospheric plasmas.

6) Microelectronic and other plasma etching at one atmosphere. A remote-exposure reactor could be used to generate etching species that are convected to a microelectronic wafer or other workpiece to be etched, in order to increase the surface energy or to improve adhesion, bonding, or other characteristics. The remote-exposure reactor would greatly increase the design flexibility of such industrial plasma processing equipment.

Illustrative Embodiments of the OAUGD Plasma Remote-Exposure Reactor

Various configurations can be used to generate a one-atmosphere uniform glow discharge plasma and use that plasma in a remote-exposure reactor. Some of these are as follows:

1) A parallel-plate OAUGD plasma generator, in which one or more pairs of parallel plates, either stacked or arranged in series, generate a OAUGD plasma between plane parallel plates. The plasma is pumped parallel to the surface of the parallel plates to accumulate active species that exit from the plasma-generation region. The active species exiting from the plasma-generation region between the parallel plates would then be convected to a remote-exposure chamber, where the active species would be utilized for plasma processing.

2) A flat-panel OAUGD plasma generator. In this embodiment, the plasma is generated by flat panels, and the active-species concentration would be increased by passing the gas flow over the surface of a succession of flat panels. The flat panels could have a plasma generated on one side only or on both sides of the flat panels, with each flat panel being operated as a single-surface OAUGD plasma generator or as a double-sided surface plasma generator, with the gas flow passing in one direction on the top of the panel, and doubling back and passing across the bottom of the panel. The flat panels could be stacked in an array of two or more, with the airflow arranged to flow in a serpentine path past all of the stacked panels, accumulating active species as it passes by each successive panel.

3) A remote-exposure chamber. The remote-exposure reactor could have a simple remote-exposure chamber downstream of the plasma-generation region. The chamber could be of any volume appropriate for the size of the workpiece(s) and the rate of generation of the active species in the plasma-generation region.

4) Ducted remote exposure. The remote-exposure reactor could consist not of an exposure chamber, but a flexible tube or duct to convey the active species-laden airflow to a workpiece. Such a workpiece might be an electronic circuit board, a plastic or fabric web, a piece of contaminated equipment or soil, or various equipment in the case of decontaminating chemical or biological agents.

5) Portable ducted remote exposure. A remote-exposure reactor could have a tube or duct as in #4 above, and be portable in the manner of a backpack, with the backpack containing rechargeable batteries, a power supply, and a stack of panels which produce active species. These active species would blow through a flexible tube in a "leaf blower" configuration, in which portability could be used to decontaminate biological or toxic chemical spills on highways or in workplaces.

6) Electrohydrodynamic pumping of airflow. The convection flow of plasma past the flat panels could be pumped by any suitable technique such as by exterior pump or blower means, by the paraelectric effect, by DC mobility drift, or by peristaltic acceleration. The last three techniques are described in further detail later in this specification. The possibility of using one or more of the later techniques to convect active species across the panels and out through an exit tube into a remote-exposure chamber or through an applicator tube or duct has a number of advantages, including the ability to pump active species from the plasma-generation region to the workpiece without moving parts, and without a requirement for additional energy input to a blower motor. These self-propelled flow-pumping mechanisms would provide an elegant engineering solution to the problem of pumping active species, since by using asymmetric rather than symmetric electrodes, for example, it would be possible to pump the gas flow using the same plasma which generates the active species, and at an insignificant additional cost in power or energy.

7) Active pumping of airflow. The self-propelled flow of air past the panels or through the parallel plates of the plasma-generation region could be accomplished by an external blower or other external means for contributing to the airflow.

Electrohydrodynamic Flow Control

Three distinct electrohydrodynamic (EHD) methods of neutral gas flow control are described in the specification. At least two of these methods may be used to provide lightweight, robust, and efficient flow pumping. These electrohydrodynamic flow control mechanisms all work at one atmosphere, for example, with a one-atmosphere uniform glow discharge plasma, although plasmas other than the OAUGD plasma and pressures other than one atmosphere may also be possible.

Electrohydrodynamics is the study of the behavior of electrically charged fluids in electric fields, and it finds application in electrostatic paint spraying and electrostatic precipitators, as well as other industrial processes. The OAUGD plasma and its related flow-control devices discussed in this specification are electrohydrodynamic in nature, and use only electric fields to produce the effects of interest. The magnetic field is typically insignificant in situations to which the OAUGD plasma is applied in this specification. An OAUGD plasma generator is an RF device that operates on displacement currents, not real currents flowing to the electrodes. This greatly reduces contamination of the plasma and the airstream associated with it by electrode material, as well as improves the integrity and lifetime of the electrodes themselves.

Unlike conventional low-pressure glow discharges operated in vacuum systems, the OAUGD plasma is a nonequilibrium "cold" plasma in which the electron kinetic temperature, number density, etc., are time dependent and follow the RF cycle of the excitation voltage. As a "cold" plasma, the electron and ion kinetic temperatures may, and usually do, differ from each other, and from the much colder neutral gas in which they are embedded. It has been shown that, throughout the RF cycle, the OAUGD plasma exhibits all the phenomenology of the classical normal glow discharge, including a negative glow, a Faraday dark space, a positive column, and a cathode region. In the cathode region, the electric field and charge density obey Aston's law. As a normal glow discharge, the OAUGD plasma operates at the Stoletow point, at which ionization in air occurs at the minimum possible energy cost of about 81 eV per ion-electron pair, and usually the OAUGD plasma operates at or near (within ±5° C.) of room temperature. Plasma torches, arc jets, and other thermal equilibrium plasmas characteristically require about 10,000 eV per ion-electron pair, at least in part because of the requirement to heat the neutral background gas to the same kinetic temperature required of the electrons to produce ionization.

The EHD effects are best studied with an individual particle rather than a continuous fluid formalism. The most productive theoretical approach to understanding the EHD effects required for flow control is the Lorentzian formalism, in which each collision of the ions or electrons gives up to the neutral background gas all the momentum and energy that they gained, on the average, since their last collision. Another conceptual aid to understanding EHD phenomena is to utilize the fact that electric field lines terminate on free charges, or on charged conductors, and that these electric field lines act like rubber bands in tension to pull charges of opposite sign together. In plasmas, including the OAUGD plasmas that give rise to flow-control effects, the polarization electric field causes the charges, the plasma, and the background gas to move toward regions with shorter electric field lines and stronger electric fields, i.e., the plasma will move paraelectrically toward increasing electric field gradients, and drag the neutral gas along with it as a result of the very frequent ion-neutral and electron-neutral collisions. In such atmospheric Lorentzian plasmas as the OAUGD plasma, the large ratio of neutrals to ions does not "dilute" the momentum lost by the ions, because the large number of collisions per second (exactly) compensates for the small ionization fraction. In atmospheric air, the ion-collision frequency is about 7 GHz; that of electrons about 5 THz. These high collision frequencies are why the electric fields are well coupled to the neutral gas through the ion/electron populations, and why the induced neutral-gas velocities can be comparable to the ion-mobility drift velocity, as will be shown below.

Paraelectric Gas Flow Control

The first of the three mechanisms that has been identified for electrohydrodynamically manipulating atmospheric plasmas and their neutral background gas is the paraelectric EHD body force. This force arises when the applied electric fields act on the net charge density of the OAUGD plasma, to provide a body force on the plasma capable of accelerating the neutral gas to velocities up to 10 meters per second. The following is a derivation of this mechanism.

The electrostatic body force on a plasma with a net charge density $\rho_c$ is given by:

$$F_E = \rho_c E \text{ newtons/m}^3 \tag{1}$$

where the net charge density $\rho_c$ is given by:

$$\rho_c = e(Zn_i - n_e) \text{ coulombs/m}^3 \tag{2}$$

where e is the fundamental electron charge, Z is the charge state of the ions, $n_i$ is the density of ions, and $n_e$ is the density of electrons in the plasma. Equation (2) is the difference between the ionic and electron number densities, and is a term that is usually ignored in quasineutral theoretical formulations. This net charge density $\rho_c$ is related to the electric field E in the plasma through Poisson's equation:

$$\nabla \cdot E = \frac{\rho_c}{\varepsilon_o} \tag{3}$$

If one substitutes Equation (3) into Equation (1), the electrostatic body force $F_E$ is:

$$F_E = \varepsilon_o E \nabla \cdot E = \frac{1}{2}\varepsilon_o \nabla \cdot E^2 \Rightarrow \frac{d}{dx}\left(\frac{1}{2}\varepsilon_o E^2\right) \tag{4}$$

The last two terms in Equation (4) are an equality for the one-dimensional formulation of interest in the present application. The expression in the parentheses in the last term of Equation (4) is the electrostatic pressure $p_E$:

$$p_E = \frac{1}{2}\varepsilon_o E^2 \text{ newtons/m}^2 \tag{5}$$

which is numerically and dimensionally the energy density, as well having the units of newtons per square meter, or pressure. In the present formulation, it is more useful to regard $p_E$ as a pressure, because of its influence on the neutral gas flow. Using Equation (5), Equation (4) may be written:

$$F_E = \frac{d}{dx}(p_E) \tag{6}$$

The body force represented by Equation (6) results because the electrostatic pressure is transmitted to the ions and electrons by acceleration in the electric field, and the momentum acquired by the ion/electrons is then transmitted in turn to the neutral gas by Lorentzian collisions.

The ordinary gasdynamic pressure $p_g$ of the neutral gas is given by:

$$p_g = nkT \tag{7}$$

where n is the neutral number denisty, k is Boltzmann's constant, and T is temperature. If viscosity forces, centrifugal forces, etc., are neglected, the body forces due to gasdynamic and electrostatic gradients will be approximately in equilibrium, as, described in Equation (8) below.

$$\nabla p_g + \nabla p_E = \frac{d}{dx}(p_g - p_E) = 0 \tag{8}$$

As a result, the sum of the gasdynamic and electrostatic pressures are approximately constant:

$$p_g - p_E = \text{constant} \tag{9}$$

Substituting Equations (5) and (7) into Equation (9), one has an approximate relation between the gasdynamic parameters and the electric field:

$$nkT - \frac{\varepsilon_o}{2}E^2 = \text{constant} \tag{10}$$

Equation (10) predicts that, in regions of high electric field ($p_E$ large), the neutral gas pressure $p_g$ is also high, reflecting a high-pressure region that will cause an outflow of gas. This pumping action is a paraelectric effect by which the plasma ions, and the neutral gas to which they are coupled by collisions, are drawn to regions of high electric field gradient.

At this point, it is useful to quantitatively compare the electrohydrodynamic forces with the viscous forces that arise in an OAUGD plasma and in the surrounding air at one atmosphere. The electrostatic pressure is given by Equation (5), and in OAUGD plasma flat panel experiments in air, such as those utilized for the gas flow pumping in this specification, the electric field is E≈10 kV/cm=10$^6$ V/m, yielding an electrostatic pressure:

$$p_E = \frac{1}{2} \times 8.85 \times 10^{-12} \times (10^6)^2 = 4.43 \text{ newtons/m}^2 \quad (11)$$

For comparison, the viscous drag on a fluid flowing over the OAUGD plasma flat plate is given by:

$$F_v^l = \frac{1}{2} C_F \rho u^2 \text{ newtons/m}^2 \quad (12)$$

where the empirical skin friction coefficient for air, $C_F$, at 300° K. is:

$$C_F = 0.0035 \quad (13)$$

The highest velocity observed in paraelectric flow acceleration experiments was u=4.0 n/sec, which when substituted into Equation (12) yields, with an air density of ρ=1.3 kg/m$^3$, a viscous drag of:

$$F_v^l = 0.036 \text{ newtons/m}^2 \quad (14)$$

Taking the ratio of the electrostatic pressure given by Equation (11) to the viscous force per unit area given by Equation (14) yields:

$$R_{vE} = \frac{p_E}{F_v^l} = \frac{4.43}{0.036} = 123 \quad (15)$$

In this case, the electrostatic pressure can produce forces more than 100 times the viscous forces acting on the neutral gas surrounding the one-atmosphere uniform glow discharge plasma.

Before leaving the subject of paraelectric EHD flow control, it is interesting to compare the forces associated with the electrostatic pressure to those which can be exerted by magnetic fields. Over a period of nearly four decades, from the mid-1950's to the mid-1990's, attempts were made to control the flow of gases around aerodynamic bodies with magnetohydrodynamic (MHD) forces. The following compares the EHD forces discussed above with the forces that can be exerted on individual charged particles, and the body forces on a plasma, by a magnetic field. First, the forces on individual charged particles are examined.

The electric field force $F_E$ on a charge e is given by:

$$F_E = eE \text{ newtons} \quad (16)$$

A magnetic field B exerts a force on a charge moving with a drift velocity $v_d$ given by:

$$F_m = e(v_d \times B) = ev_d B \quad (17)$$

The ratio of these two forces, for a single charge, is found by dividing Equation (16) by Equation (17), to yield:

$$R_{Ems} = \frac{F_E}{F_m} = \frac{E}{v_d B} \quad (18)$$

In the OAUGD plasma, the electric field is a minimum of about 10$^6$ V/m, and a reasonable value for a magnetic field at the surface of the panel due to permanent magnets is approximately B=0.5 tesla. In certain applications described in this specification in which the flowing gas would be used for decontamination or sterilization purposes, flow velocities much above 30 miles per hour (12 m/sec) are not likely to be encountered. Using this as the characteristic velocity in Equation (18), a ratio of the electric field force to the magnetic field force on a charged particle is given by:

$$R_{Ems} = \frac{10^6}{12 \times 0.5} = 167,000 \quad (19)$$

Thus, in this situation, the electric field force on a charge is more than one hundred thousand times that exerted by a magnetic field of reasonable magnitude on that same charge.

To compare the EHD and MHD body forces acting in a situation of interest in this specification, the magnetic body force can be written as:

$$F_m = J \times B \text{ newtons}/m^3 \quad (20)$$

If a current density of 1 amp/cm$^2$, or 104 amps/m$^2$ is assumed, which is the upper limit of glow discharges at the glow-to-arc transition, and if it is further assumed that a magnetic induction of 0.5 tesla is generated on the surface by permanent magnets, the magnetic body force is:

$$F_m = JB = 5000 \text{ newtons}/m^3 \quad (21)$$

The electrostatic body force is given by Equation (4), and may be written:

$$F_E = \nabla p_E = \frac{d}{dx}\left(\frac{\varepsilon_o E^2}{2}\right) = \varepsilon_o E \frac{dE}{dx} \quad (22)$$

Again assuming for the OAUGD plasma an electric field of E=10$^6$ V/m, ΔE=10$^6$ V/m, and Δx=0.5 mm, the electrostatic body force is approximately:

$$F_E = 8.85 \times 10^{-12} \times \frac{10^{12}}{5 \times 10^{-4}} = 1.77 \times 10^4 \text{ newtons}/m^3 \quad (23)$$

By taking the ratio of Equation (23) to Equation (21), the ratio of the electrostatic body force to the magnetic body force in this example is about 3.5, again indicating the potentially larger magnitude of the electrohydrodynamic body forces (and effects), as compared to that of the MHD body forces.

From the above discussion, a number of factors favor flow control based on paraelectric and related EHD effects: 1.) When compared to a static magnetic field, the electric field of force is preferable, because a static magnetic field cannot do work on a particle or a plasma, but the electric field can do so. 2.) The EHD forces can be made significantly greater than viscosity forces for OAUGD plasma applications such as the decontamination reactors discussed in this specification. 3.) EHD forces are greater than or comparable to MHD forces for situations of interest in this specification. 4.) Past attempts to use MHD forces to produce acceleration of gasdynamic flows have often failed to be of practical interest because the electrical conductivity is not sufficiently large. The electrical conductivity a is given by:

$$\sigma = \frac{e^2 n_e}{m_e \nu_{en}} \Big/ \text{ohm-m} \tag{24}$$

This conductivity is proportional to the electron number density $n_e$, which in most plasmas operated at one atmosphere is too low to produce electrical conductivities of useful magnitudes. With the EHD body forces, the key parameter is the net charge density $\rho_c$, given by Equation (2). It is generally much easier to achieve an interesting value of $\rho_c$ to produce EHD effects than it is to achieve adequate values of $n_e$ to produce MHD effects of interesting magnitudes. In EHD devices, including OAUGD plasma generators, number densities below $10^{16}$ electrons per cubic meter can yield high electric fields, strong EHD body forces, and interesting flow effects.

Another potential advantage of the paraelectric EHD flow acceleration mechanism, implied by the balance of gasdynamic and electrostatic pressures described in Equation (10), is that the electric fields can be set up with a very simple, robust, and lightweight system of electrodes. Such a flow-acceleration mechanism involves no moving parts, and, as long as an air plasma is used, it requires no external input gases or liquids, nor does it produce any solid waste or unwanted byproducts, other than the species that are used to provide decontamination/sterilization of the surfaces treated. A flow acceleration mechanism using an OAUGD plasma therefore offers the potential advantages of a unit without moving parts, with potentially great reliability, and lightness of weight. In such a unit, the OAUGD plasma not only provides the active species to effect decontamination or sterilization, but it also provides the means by which the gas flow can be pumped to the surface being decontaminated.

Exploratory Experiments With Paraelectric Gas Flow Acceleration

Figure 1A:
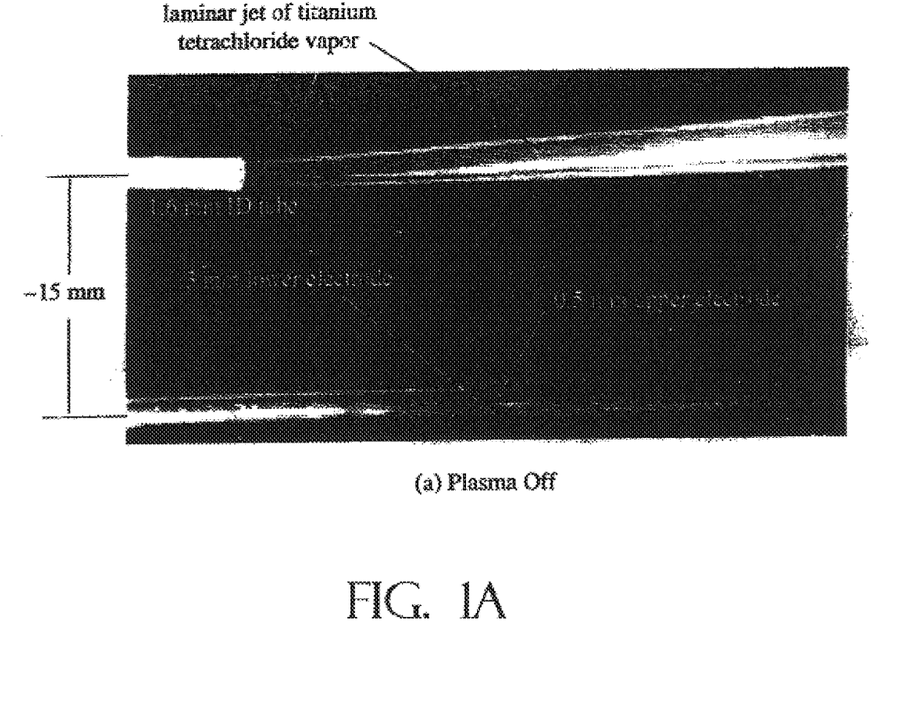
FIGS. 1(a) and 1(b) show the influence of a OUAGD plasma on a laminar jet of smoke injected in still air above a single, asymmetric electrode arrangement where the plasma is off and on, respectively.
Figure 1B:
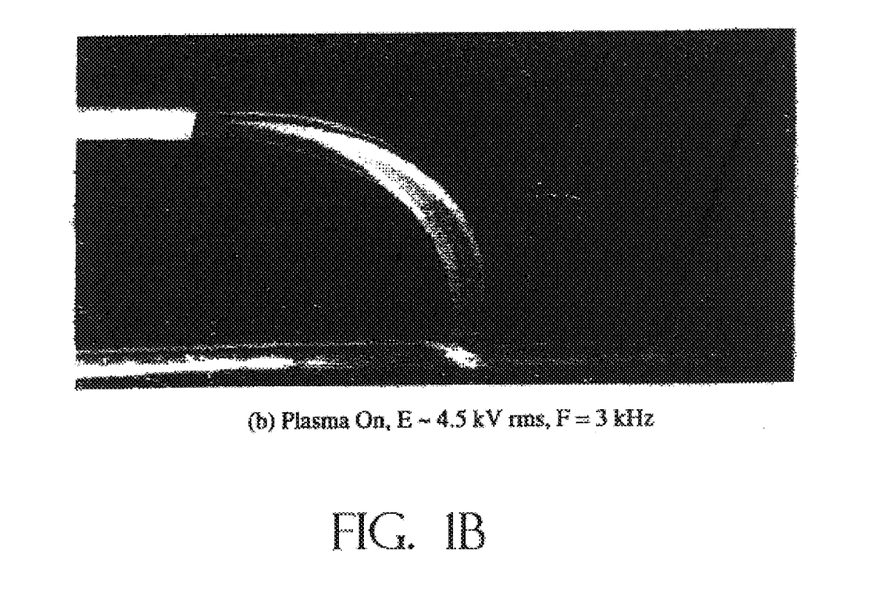
Figure 2A:
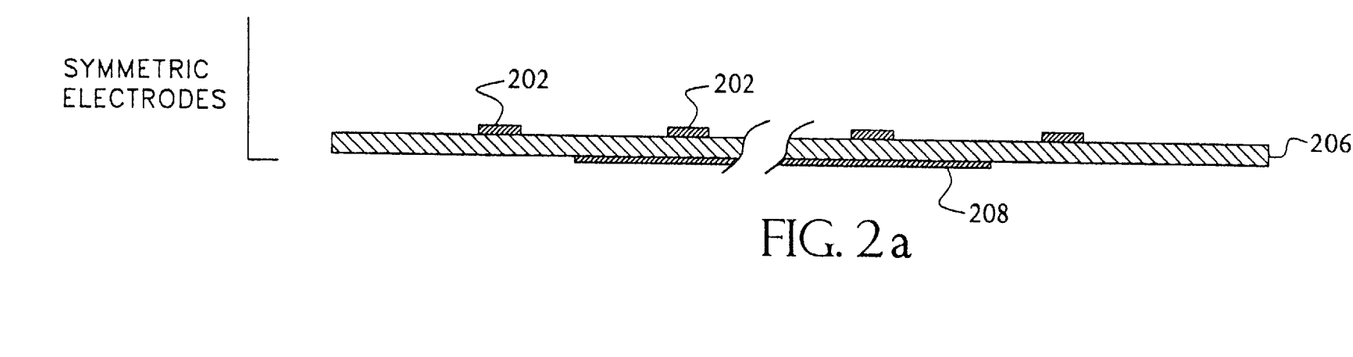
FIGS. 2(a)–(b) show cross-sectional views of symmetric and asymmetric embodiments of a plasma panel, respectively.
Figure 2B:
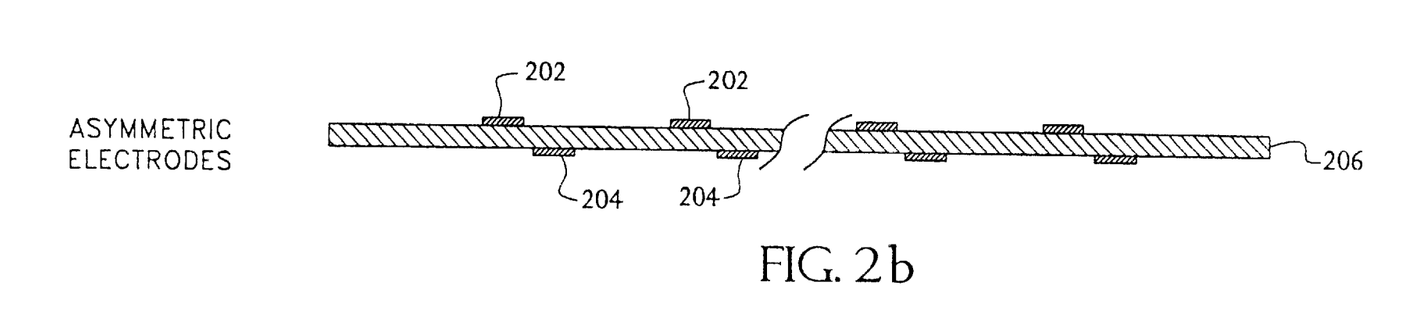

FIGS. 1(a)–(b) show digital images of a smoke flow test. In FIG. 1(a), a jet of low-velocity smoke flows horizontally 1.5 cm above a surface with an unenergized electrode located on it. In FIG. 1(b), the electrode is energized. The geometry of the electrode is shown in FIG. 2(b), where the electrode in FIGS. 1(a)–(b) is part of an upper array of strip electrodes 202 that are positioned asymmetrically relative to a lower array of strip electrodes 204 located on the opposite side of a dielectric substrate 206 separating the two arrays. The geometry is asymmetric in such a way that the neutral gas flow is pumped to the left with a velocity of a few meters per second. The descent of the smoke jet to the surface in FIG. 1(b) occurs because of the low-pressure region generated by the paraelectric effects discussed above in the vicinity of the plasma. In FIG. 1(b), the plasma is localized in a small region near the electrode.

In interpreting these digital images, it is important to realize that the smoke consists of titanium dioxide particles, a standard flow visualization technique used in the field of aerodynamics. The particles are not charged, and the smoke serves only as a passive flow marker. Furthermore, electrophoretic or dielectrophoretic effects involving the smoke are much too small to produce the observed deflection of the gas jet. Increased or decreased velocities, and other aerodynamic phenomena observed in tests (such as vortex formation) exist whether or not the smoke is present. In this case, the presence of an OAUGD plasma results in the EHD-induced flow acceleration. The mere presence of a strong electric field without a plasma present is not sufficient to produce the induced flow velocities. In the digital image shown in FIG. 1(b), the (blue) glow of the plasma is completely washed out by the strong illumination needed to observe the smoke. The plasma itself is confined to within about 1–2 mm of the plasma surface, and extends no more than about 5 millimeters from the asymmetric electrode shown in FIG. 2(b).

Theory of EHD-Induced Flow by Paraelectric Effects

A simple theory has been formulated to quantitatively derive the velocity due to paraelectric gas flow acceleration effects that are produced by the OAUGD plasma. The electrostatic pressure is given by Equation (5) above, and this will accelerate the neutral gas to a velocity $v_o$ which will lead to a stagnation pressure $p_S$ equal to the electrostatic pressure:

$$p_S = \frac{1}{2}\rho v_o^2 = \frac{1}{2}\varepsilon_o E^2 \tag{25}$$

In Equation (25), it has been assumed that the electrostatic pressure compresses the gas to a stagnation (or dynamic) pressure given by the middle term of the equation. When the gas is accelerated, a time-reversed version of stagnated gas flow will occur. Solving Equation (25) for the induced neutral gas flow velocity $v_o$, one obtains:

$$v_o = E\sqrt{\frac{\varepsilon_o}{\rho}} \text{ m/sec} \tag{26}$$

The induced neutral gas flow velocity is a function of the mass density of the working gas (1.3 kg per cubic meter for atmospheric air at standard temperature and pressure (STP)), and it is also a function of the electric field E. In the OAUGD plasma, the electrode geometry is fixed, and hence the electric field (and the flow velocity) are directly proportional to the applied voltage. In the OAUGD plasma flat panel used in the flow-visualization experiments, the electric field E is approximately $10^6$ V/m. When these values of electric field and mass density are substituted into Equation (26), a predicted neutral gas flow velocity is obtained as:

$$v_o = 10^6 \sqrt{\frac{8.854 \times 10^{-12}}{1.3}} = 2.6 \text{ meters/sec} \tag{27}$$

Figure 3:
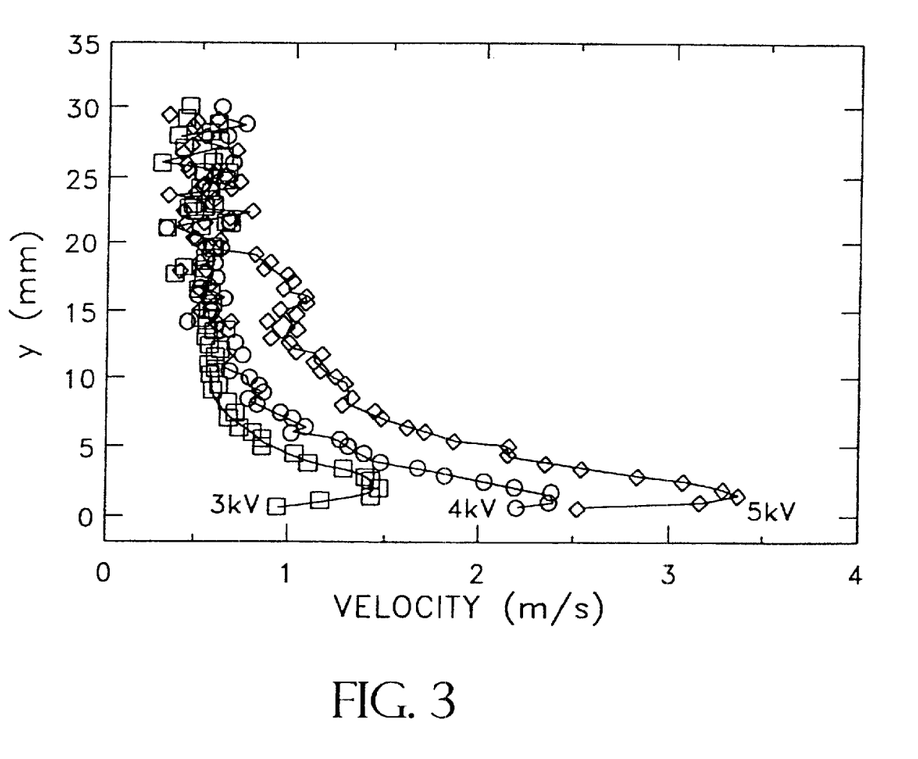
FIG. 3 shows blowing velocity profiles for an asymmetric plasma panel mounted in a wind tunnel without flow.
Figure 4:
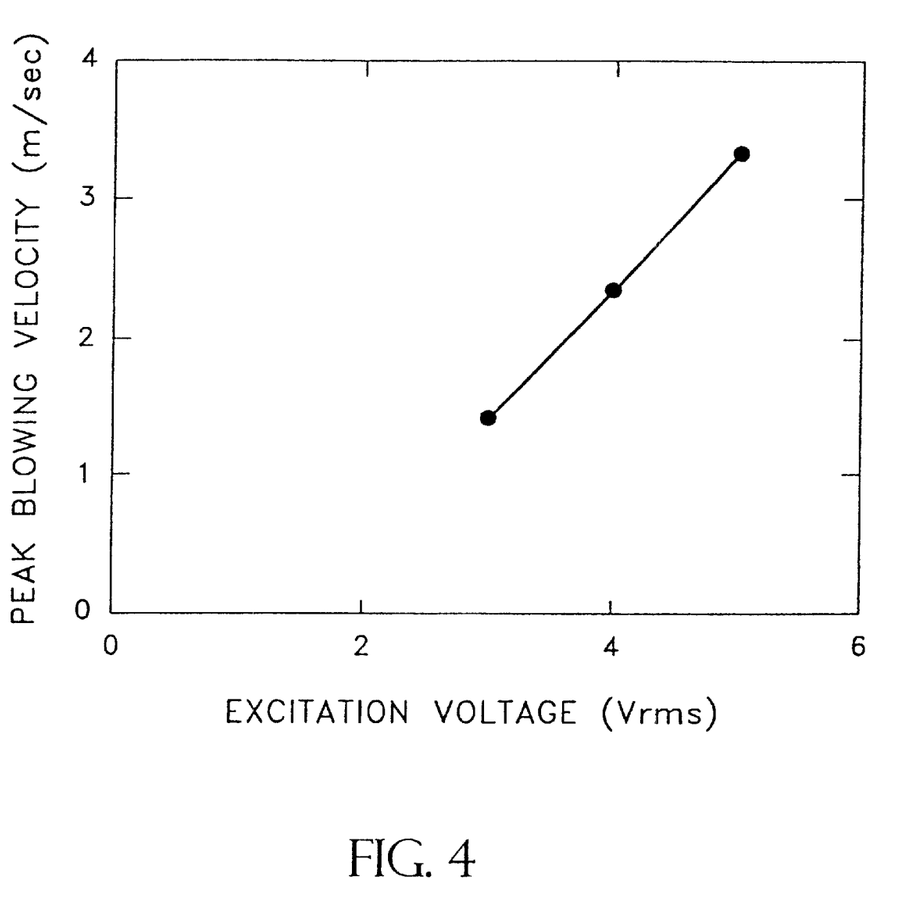
FIG. 4 shows a graphical representation of the maximum blowing velocities of FIG. 3 plotted as a function of the excitation voltage.

The blowing velocities near the surface of a panel covered with asymmetric electrodes similar to those in FIGS. 1(b) and 2(b) were measured with a pitot tube above the surface of the panel, and are plotted in FIG. 3. The maximum velocities observed with the pitot tube are shown plotted in FIG. 4, as a function of the excitation voltage. This figure shows induced neutral gas velocities of several meters per second, consistent with Equation (27), and it shows that, above a threshold voltage at which the plasma initiates, the neutral gas velocity is directly proportional to the excitation voltage, again consistent with the linear dependence on electric field predicted by Equation (26).

EHD Convection Induced by DC Mobility Drift

The second of three EHD-related neutral gas flow acceleration mechanisms available to pump the gas flow in a decontamination/sterilization reactor relates to the flow velocities induced by Lorentzian collisions of either electrons or ions as they drift in a DC electric field imposed along the surface of a flat panel containing strip electrodes. Such a panel is illustrated in FIG. 2(a), in which the bottom of the panel is a solid copper ground plane 208, and the top of the panel consists of a number of parallel strip electrodes 202 connected to a low-frequency RF power supply (not shown) to create the OAUGD plasma. These electrodes also are connected to a DC power supply that maintains an electric field along the panel, perpendicular to the axis of the individual electrodes. This DC electric field causes ions and electrons to drift (in opposite directions). As they drift, they transfer momentum to the neutral gas as a result of their Lorentzian collisions. The Lorentzian term for the loss of momentum by individual electrons in a DC electric field is:

$$mv_{de}v_{en} \text{ kg-m/sec}^2 \tag{28}$$

The volumetric Lorentzian momentum loss is given by multiplying Equation (28) by the electron number density $n_e$:

$$M_e = m n_e v_{de} v_{en} \text{ kg-m/sec}^2\text{-m}^3 \tag{29}$$

where $v_{de}$ is the electron drift velocity and $$V_{en} = n_o \langle\sigma v\rangle_{ne} \text{ electron collisions/sec} \tag{30}$$

is the electron collision frequency. By combining Equations (29) and (30), one obtains:

$$M_e = m v_{de} n_o n_e \langle\sigma v\rangle_{ne} = m v_{de} R_{ne} \tag{31}$$

where $R_{ne}$ is the volumetric reaction rate, the total number of electron-neutral collisions per second and per cubic meter. Equation (31) will be exactly equal to the momentum transferred by the electrons to the neutral population, which is:

$$M_o = M_o n_o v_{oe} v_{ne} \tag{32}$$

where the neutral collision frequency with the electrons is given by $$v_{ne} = n_e \langle\sigma v\rangle_{ne} \tag{33}$$

Combining Equations (32) and (33), one obtains:

$$M_o = M_o v_{oe} n_o n_e \langle\sigma v\rangle_{ne} = M_o v_{oe} R_{ne} \tag{34}$$

where $M_o$ is the neutral mass (28.5 for air), and $v_{oe}$ is the electron drift-induced neutral convection velocity. Equations (31) and (34) are equal, so that:

$$M_o = M_o v_{oe} R_{ne} = M_e = m v_{de} R_{ne} \tag{35}$$

from which it follows that the neutral gas velocity due to the electron momentum transfer to the neutral atoms is given by:

$$v_{oe} = \frac{m v_{de}}{M_o} \tag{36}$$

Equation (36) states that the electron-induced neutral gas drift velocity is equal to the electron mobility drift velocity, modified by the ratio of the electron mass to the average neutral atom mass. The electron mobility drift velocity can be written in terms of the electric field and the electron mobility as:

$$v_{de} = \mu_e E = \frac{eE}{m v_{ec}} \text{ m/sec} \tag{37}$$

Further substituting Equation (37) into Equation (36), one has an expression for the induced neutral gas velocity due to electron-neutral momentum transfer:

$$v_{oe} = \mu_e E = \frac{eE}{M_o v_{ec}} \text{ meters/sec} \tag{38}$$

In one implementation, $E=10^6$ V/m, $M_o=28.5$ $m_p$, $e/m_p=9.56\times10^7$, $v_{ec}=5.32\times10^{12}$/sec. Substituting these values into Equation (38), one obtains:

$$v_{oe} = 0.63 \text{ meters/sec} \tag{39}$$

The neutral gas velocity due to electron-neutral collisions is relatively small, and less than that due to the paraelectric effects previously analyzed and described by Equation (26). This low velocity is a consequence of the electron/neutral atom mass ratio appearing in Equations (36) and (38).

The EHD flow velocity induced by DC mobility drift of ions is examined next. By analogy with Equation (29) for electrons, the Lorentzian volumetric momentum loss term for ions is given by:

$$M_i = M_i n_i v_{di} v_{in} = M_i v_{di} R_{ni} \tag{40}$$

where $v_{di}$ is the ion drift velocity. If heating, viscous, and centrifugal effects are ignored, this momentum is transferred from the ions to the neutral population to induce a neutral gas convection velocity $v_{oi}$. The neutral momentum acquired from Lorentzian collisions with ions is given by:

$$M_o = M_o v_{oi} M_o v_{ni} = M_o v_{oi} R_{ni} \tag{41}$$

The ion mobility drift velocity is given by:

$$v_{di} = \mu_i E = \frac{eE}{M_i v_{in}} \text{ meters/sec} \tag{42}$$

Equating Equations (40) and (41), and substituting in Equation (42), one obtains for the neutral gas velocity induced by ion-neutral momentum transfer:

$$v_{oi} = \frac{M_i v_{di}}{M_o} = \frac{eE}{M_o v_{in}} \tag{43}$$

In this case, the neutral gas drift velocity is essentially equal to the ion mobility drift velocity, since the ion mass in the numerator, and the neutral atom mass in the denominator, are the same when the ions are formed from the neutral background working gas. For air, $E=10^6$ V/m, $M_o=28.5$ $m_p$, $e/m_p=9.56\times10^7$, $v_{in}=7\times10^9$ yields an induced gas flow velocity of:

$$v_{oi} = 480 \text{ meters/sec} \tag{44}$$

This velocity is greater than Mach one for air (about 333 m/sec), but heating and viscous effects will reduce this to lower values. This method of imparting a net velocity to air will not be practical for some applications, because the necessary electric fields, on the order of $10^4$ V/cm, require high voltages which may be hazardous to someone using such a device.

EHD Flow Acceleration by Peristaltic Excitation of Strip Electrodes

Figure 5:
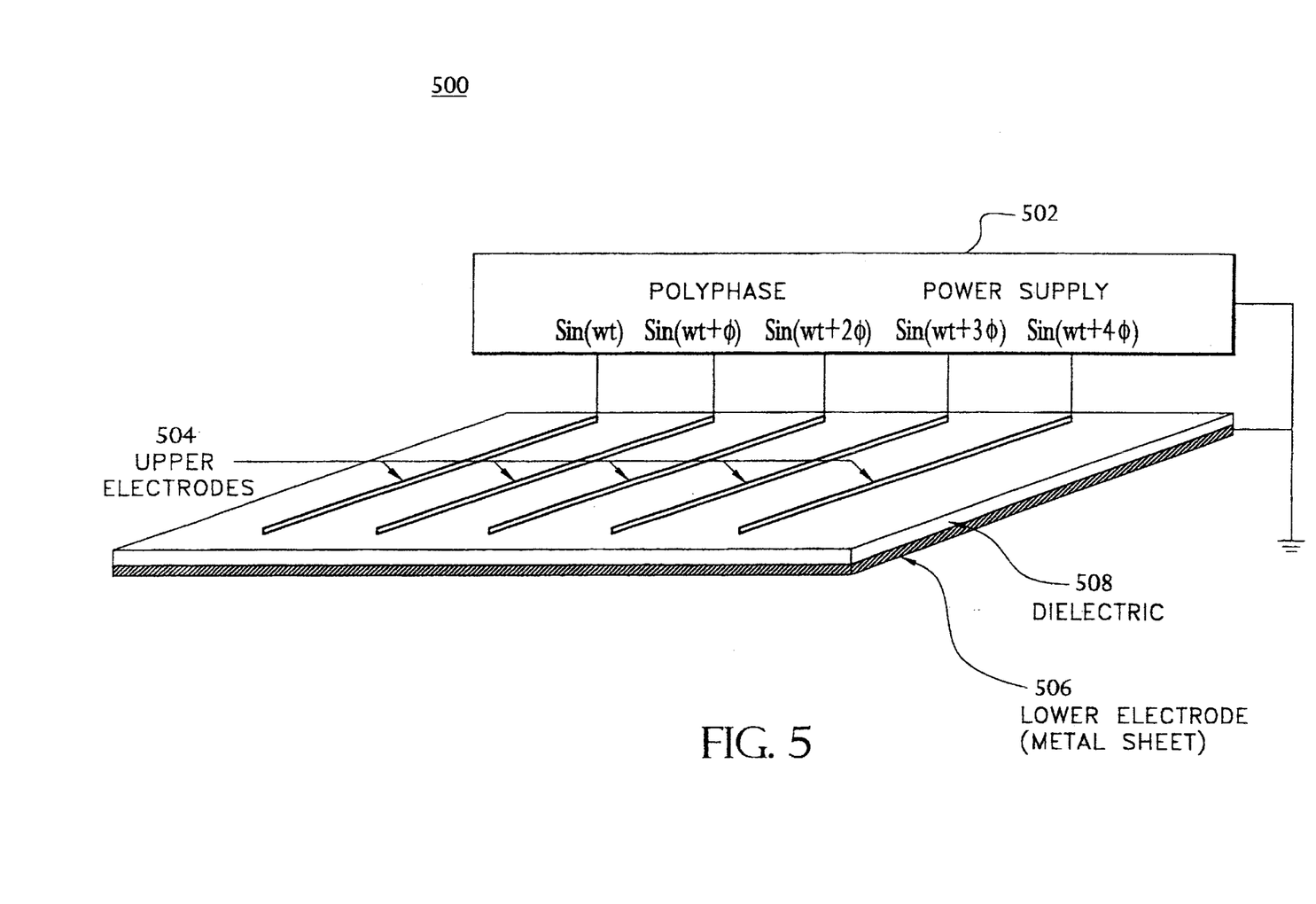
FIG. 5 shows the plasma panel of FIG. 2(a) configured for peristaltic plasma generation.

FIG. 5 shows a peristaltic plasma accelerator 500 that avoids certain disadvantages of a DC electric field. Accelerator 500 comprises a polyphase RF power supply 502 that applies power to an array of upper strip electrodes 504 separated from a lower sheet electrode 506 by a dielectric substrate 508. In this configuration, the RF power that generates the OAUGD plasma is provided by polyphase RF power supply 502 such that successive electrode strips 504 are energized at progressively increasing phase angles, like the individual lights on a theater marquee. Because the individual strips are turned on with a phase angle which increases (in FIG. 5) from left to right, the effect is that of a traveling wave from left to right. In an OAUGD plasma panel, the traveling wave will convect the plasma and the neutral gas along with it. This gas flow concept is covered by U.S. Pat. No. 5,669,583.

Consider the strip electrodes in FIG. 5, each spaced L meters apart and each with a phase angle 360°/N with respect to adjacent electrodes. A traveling (peristaltic) wave of voltage propagates to the right, given by:

$$V = V_o \, \text{SIN}(\omega t - kx) \text{ volts} \tag{45}$$

where the wave number of the electrostatic wave is:

$$k = \frac{2\pi}{\lambda} = \frac{2\pi}{NL} \, m^{-1} \tag{46}$$

In Equation (46), N is the number of electrodes per cycle, and the phase angle $\phi$ is given by:

$$\phi = \frac{360°}{N} \tag{47}$$

The phase velocity which acts on the net charge density is given by:

$$v_p = \frac{\omega}{k} = \frac{2\pi v_o NL}{2\pi} = v_o NL \tag{48}$$

where $v_o$ is the driving frequency in hertz. For example, $v_o$=3000 Hz, N=8, L=$10^{-2}$ m=1cm. For these values, $$v_p = 240 \text{ m/sec} \tag{49}$$

giving a phase velocity for these characteristic operating conditions of a few hundred meters per second. In order for the ions to be able to keep up with this traveling wave, the ion mobility drift velocity has to be of the same magnitude.

The peristaltic electric field which drags the ions and the neutral gas along the surface is given by:

$$E = -\nabla V = -\frac{dV}{dx} = +V_o k \cos(\omega t - kx) \tag{50}$$

The ions will "snowplow" to the maximum electric field drift velocity by a modification of the diocotron instability. The maximum electric field from Equation (50) is given by:

$$E_{\max} = \frac{2\pi V_o}{NL} \text{ volts/meter} \tag{51}$$

The previous derivation of Equation (43) has shown that the ion drift velocity will equal the ion-induced neutral convection velocity, or:

$$v_{oi} = v_{di} = \mu_i E_{\max} = \frac{e}{M_i v_{in}} \times \frac{2\pi V_o}{NL} \text{ meters/sec} \tag{52}$$

For best effect, this ion-induced neutral convection velocity and ion drift velocity should be approximately equal to the peristaltic phase velocity of Equation (49). Using V=3000 volts, $e/m_p$=9.56×$10^7$, one obtains an induced neutral gas drift velocity:

$$v_{oi} = \frac{9.56 \times 10^7 \times 2\pi \times 3 \times 10^3}{28.5 \times 7 \times 10^9 \times 10^{-2} \times 8} = 113 \text{ meters/sec} \tag{53}$$

This velocity also ignores viscosity, heating, and other real gas effects, but corresponds to a velocity of about 270 miles per hour. It should not be difficult to adjust the operating parameters of the OAUGD plasma to reduce these velocities to those appropriate for a wide range of aerodynamic applications.

Remote-Exposure Reactors

Figure 6:
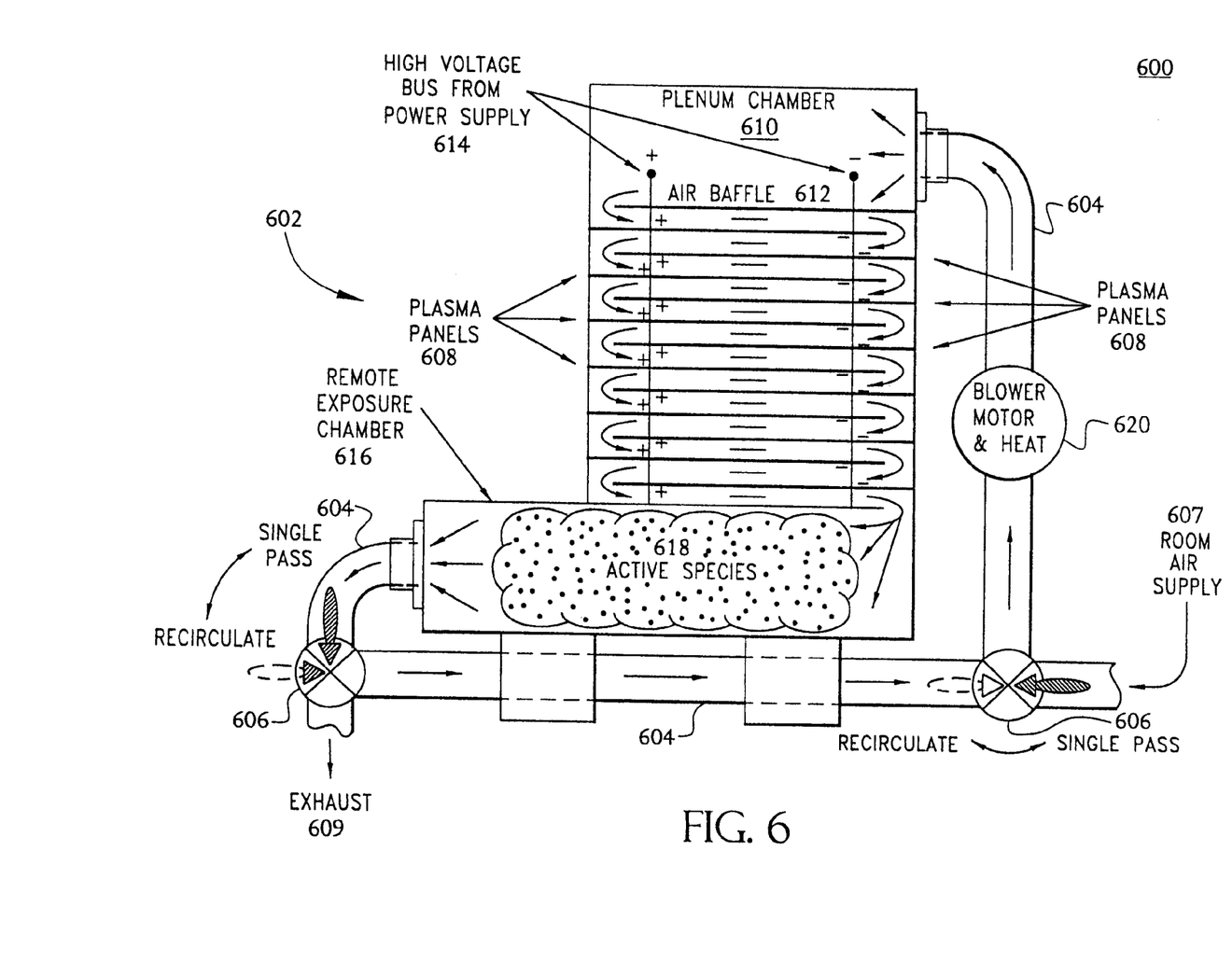
FIG. 6 shows a schematic view of a remote-exposure reactor, according to one embodiment of the present invention.

FIG. 6 shows a schematic view of a remote-exposure reactor 600, according to one embodiment of the present invention. The outline of remote-exposure reactor 600 represents a Plexiglas chamber 602, which is outfitted with two-inch diameter plastic tubes 604 with valves 606 that allow either the airflow to be recirculated continuously through the remote-exposure reactor or fresh incoming air 607 to pass once through the reactor and then exhaust (609) out of the reactor. Inside this remote exposure reactor are shown, at the top, a stacked series of flat panels 608, similar to the panel shown in FIG. 2(*b*), each of which can generate on both its upper and lower surfaces a two-dimensional flat OAUGD surface plasma. These individual panels are stacked in a vertical array and are displaced alternately in such a way within a baffle system 612 that the airflow entering from the upper plenum chamber 610 follows a serpentine, zig-zag path past the series of panels as the airflow travels from the top to the bottom of the stack. The airflow proceeds past these panels, all of which are energized via leads 614 by an external power supply (not shown), and ultimately discharges into the lower remote-exposure chamber 616, where the active species 618 that are convected from the plasma panels interact with one or more workpieces located within the remote-exposure chamber. The airflow then flows out of the remote-exposure reactor, or is recirculated back past the plasma panels. This recirculation can increase the concentrations of those active species which have a lifetime longer than the time required to pass once around the airflow system shown in FIG. 6. Optional blower motor/heater 620 can be provided to assist in moving and/or heating the air as it circulates through the remote-exposure reactor.

Figures 7A, 7B:
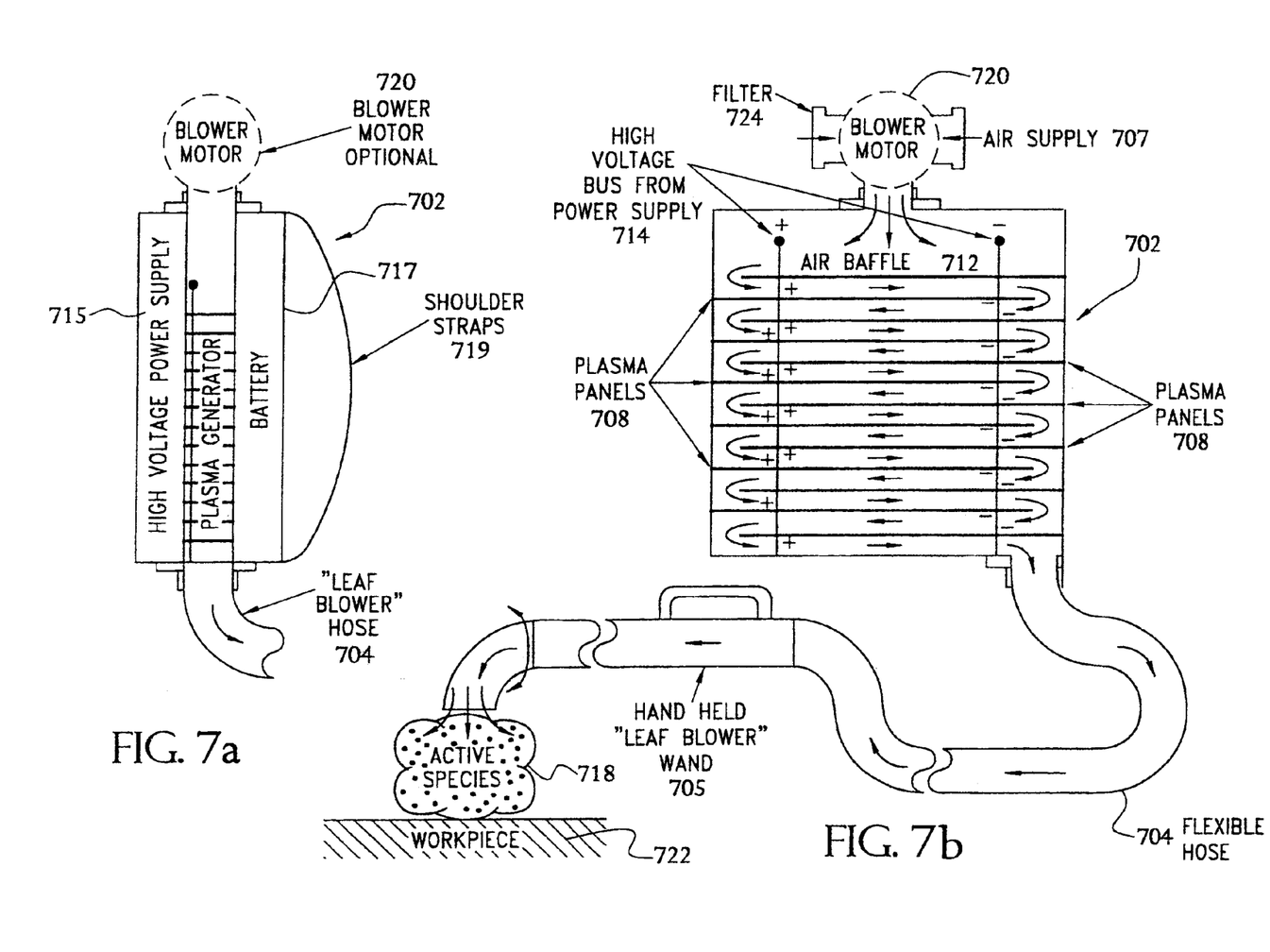
FIG. 7(a) shows a schematic view of a backpack-type remote-exposure reactor, according to another embodiment of the present invention.
FIG. 7(b) shows a cutaway side view of the reactor of FIG. 7(a).

FIG. 7(*a*) shows a schematic view of a remote-exposure reactor 700, according to another embodiment of the present invention. FIG. 7(*b*) shows a cutaway side view of reactor 700. Reactor 700 is a portable backpack unit that might be used to deal with chemical or biological agents, or hazardous civilian spills of biohazards or toxic chemicals in workplaces or on public highways. In this case, the reactor comprises a backpack 702 containing a series of flat panels 708 arrange in an air baffle 712, a rechargeable battery 717, and a high voltage RF power supply 715 connected to the panels at leads 714. This portable backpack unit with shoulder straps 719 might pump the airflow required to carry the decontaminating or sterilizing active species to the workpiece by use of paraelectric or peristaltic EHD effects, with possible assistance from an optional blower motor 720 to pull air from an air supply 707 through filters 724. The airflow would be conducted to the workpiece 722 through a flexible tube 704 with a hand-held wand 705, like a leaf blower, to direct active species 718 onto the contaminated surface.

In both FIGS. 6 and 7, the flat panels used to generate the active species could have asymmetric electrodes as in FIG. 2(b) that could accelerate the gas flow using the paraelectric effects described earlier, or the flat panels could have a series of electrode strips as in FIGS. 2(a) and 5 driven by polyphase RF power that could peristaltically accelerate the neutral gas flow to higher velocities than the paraelectric EHD effects. In either case, the blower motor is optional, and the same plasma which produces the active species would also pump the airflow either into the remote exposure chamber, or into the flexible hose where it is conveyed to the workpiece.

The present invention can also be implemented using alternative embodiments of the remote-exposure reactor. The plasma can be generated in a controlled gas atmosphere, in which the gas can be a gas such as air, or helium, argon, mixtures of helium and/or argon with oxygen, or mixtures with air. Since the areas where the workpiece is exposed to the active species is remote from the plasma generation areas, the gas in the area of the workpiece can be any gases as desired, including gases which are suitable for modifying the surface of the workpiece and/or normally would not be used in conjunction with the plasma generation. In addition, the gas can flow from bottom to top rather than from top to bottom. Similarly, the remote-exposure reactor can have a row of vertical flat panels rather than a column of horizontal flat panels, as in FIGS. 6 and 7. Of course, the panels can also be implemented with orientations other than horizontal or vertical. Although it may not be as practical for some applications, the self-propelled plasma can be generated using the DC mobility drift technique instead of, or in addition to, either of the paraelectric or peristaltic techniques.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An apparatus comprising:
   (a) a plasma generator configured to generate an atmospheric plasma in a working gas within a plasma-generation region and convect one or more active species of the plasma away from the plasma-generation region; and
   (b) flexible tubing configured to convey the one or more active species away from the plasma-generation region; and
   (c) a hand-held wand configured to receive the one or more active species from the tubing and to enable an operator to move the wand to direct the one or more active species onto a workpiece located outside of the apparatus.

2. The apparatus of claim 1, wherein the tubing is configured with one or more valves to recirculate at least a portion of the one or more active species back to the plasma-generation region to increase concentration of at least one of the active species.

3. The apparatus of claim 1, wherein the plasma generator is configured as part of a portable unit.

4. The apparatus of claim 3, wherein the portable unit is configured to be worn by the operator as a backpack.

5. The apparatus of claim 1, further comprising a blower configured to provide the working gas to the plasma-generation region and convect the one or more active species away from the plasma-generation region.

6. The apparatus of claim 1, wherein the plasma generator is configured to generate a self-propelled plasma.

7. The apparatus of claim 1, wherein the plasma generator comprises one or more plasma panels adapted to configured to a power supply to generate the plasma.

8. The apparatus of claim 7, wherein the plasma generator comprises a plurality of plasma panels configured in an air baffle such that the one or more active species are convected in a serpentine manner through the plasma-generation region.

9. The apparatus of claim 1, wherein the working gas is air at one atmosphere.

10. The apparatus of claim 9, wherein the plasma is an OAUGDP (one-atmosphere uniform glow discharge plasma).

11. The apparatus of claim 1, wherein the active species are oxidizing species carried within a low heat flux of the plasma.

12. The apparatus of claim 11, wherein the active species are atomic oxygen, ozone or nitrogen oxides.

* * * * *

UNITED STATES PATENT AND TRADEMARK OFFICE
CERTIFICATE OF CORRECTION

PATENT NO. : 6,676,802 B2
DATED : January 13, 2004
INVENTOR(S) : J. Reece Roth

It is certified that error appears in the above-identified patent and that said Letters Patent is hereby corrected as shown below:

<u>Title page,</u>
Item [30], Foreign Application Priority Data, replace "PCT/US99/00430" should read -- PCT/US99/00480 --.

Signed and Sealed this

Twenty-third Day of March, 2004

JON W. DUDAS
*Acting Director of the United States Patent and Trademark Office*